US009708436B2

(12) United States Patent
Burdeniuc et al.

(10) Patent No.: US 9,708,436 B2
(45) Date of Patent: Jul. 18, 2017

(54) TERTIARY AMINE COMPOSITION AND METHOD FOR MAKING THE COMPOSITION

(71) Applicant: EVONIK DEGUSSA GMBH, Essen (DE)

(72) Inventors: Juan Jesus Burdeniuc, Colmar, PA (US); Jennifer Elizabeth Antoline Al-Rashid, Allentown, PA (US); Andrew Wilson Wang, Macungie, PA (US); Diana Sue Dunn, Fogelsville, PA (US); You-Moon Jeon, Breinigsville, PA (US); Jane Garrett Kniss, Kempton, PA (US); Stephan Hermann Wendel, Oldenburg (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 15/055,744

(22) Filed: Feb. 29, 2016

(65) Prior Publication Data

US 2016/0222153 A1 Aug. 4, 2016

Related U.S. Application Data

(62) Division of application No. 13/633,423, filed on Oct. 2, 2012, now Pat. No. 9,273,175.

(60) Provisional application No. 61/542,405, filed on Oct. 3, 2011.

(51) Int. Cl.

| | |
|---|---|
| ***C08G 18/18*** | (2006.01) |
| ***C07C 209/84*** | (2006.01) |
| ***C08G 18/20*** | (2006.01) |
| ***C08G 18/63*** | (2006.01) |
| ***C08G 18/76*** | (2006.01) |
| ***C08G 18/12*** | (2006.01) |
| ***C08G 18/40*** | (2006.01) |
| ***C08G 18/65*** | (2006.01) |
| ***C08G 18/08*** | (2006.01) |
| ***C08J 9/14*** | (2006.01) |
| *C08G 101/00* | (2006.01) |

(52) U.S. Cl.

CPC ........ *C08G 18/1833* (2013.01); *C07C 209/84* (2013.01); *C08G 18/12* (2013.01); *C08G 18/14* (2013.01); *C08G 18/18* (2013.01); *C08G 18/1825* (2013.01); *C08G 18/20* (2013.01); *C08G 18/2054* (2013.01); *C08G 18/4072* (2013.01); *C08G 18/632* (2013.01); *C08G 18/657* (2013.01); *C08G 18/7621* (2013.01); *C08J 9/14* (2013.01); *C08G 2101/005* (2013.01); *C08G 2101/0008* (2013.01); *C08G 2101/0083* (2013.01); *C08J 2203/06* (2013.01); *C08J 2375/04* (2013.01); *C08J 2375/08* (2013.01)

(58) Field of Classification Search

CPC . C08G 18/18; C08G 18/1833; C08G 18/2054

See application file for complete search history.

(56) References Cited

U.S. PATENT DOCUMENTS

| | | | |
|---|---|---|---|
| 4,394,491 | A | 7/1983 | Hoffman |
| 4,801,426 | A | 1/1989 | Borland et al. |
| 7,169,268 | B2 | 1/2007 | Su et al. |
| 7,879,928 | B2 | 2/2011 | Goh et al. |
| 2008/0269382 | A1 | 10/2008 | Gerster et al. |
| 2009/0088489 | A1 | 4/2009 | Terheiden et al. |
| 2011/0009512 | A1 | 1/2011 | Grigsby, Jr. et al. |

FOREIGN PATENT DOCUMENTS

| | | | |
|---|---|---|---|
| JP | 2004057296 | A | 2/2004 |
| WO | 01/58976 | A1 | 8/2001 |
| WO | 03/016372 | A1 | 2/2003 |
| WO | 03/016373 | A1 | 2/2003 |
| WO | 03/055930 | A1 | 7/2003 |
| WO | 2004/060956 | A1 | 7/2004 |
| WO | 2006111492 | A2 | 10/2006 |
| WO | 2006/116456 | A1 | 11/2006 |
| WO | 2011/084865 | A1 | 7/2011 |

*Primary Examiner* — Michael L Leonard

(74) *Attorney, Agent, or Firm* — Andrew H. Chung; Linda S. Li; Jason S. Ngui

(57) ABSTRACT

A composition and method for producing a tertiary amine is disclosed. The tertiary amine is contacted with an inert gas. The inert gas is nitrogen or more preferably argon. The amine composition is useful in producing polyurethane foam with lower levels of chemical emissions particularly lower emissions of toxic chemicals.

18 Claims, 1 Drawing Sheet

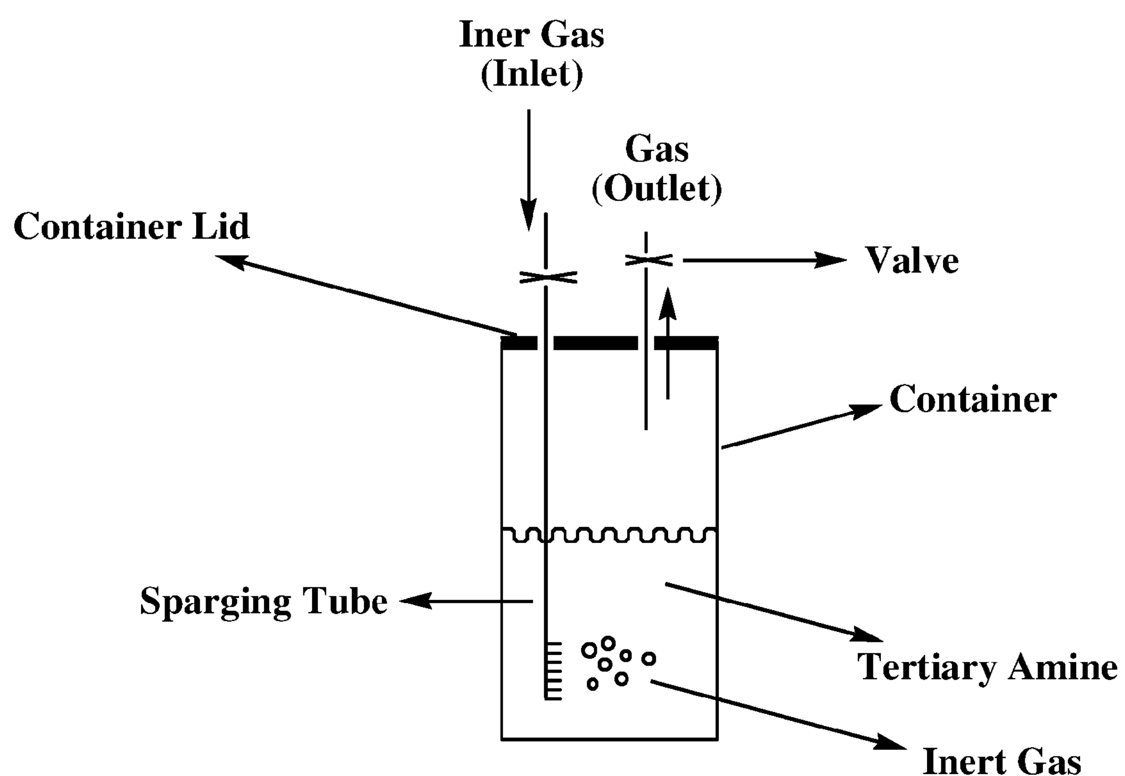
*Schematic Representation of Equipment*

TERTIARY AMINE COMPOSITION AND METHOD FOR MAKING THE COMPOSITION

CROSS-REFERENCE TO RELATED APPLICATIONS

This Application is a divisional application of U.S. application Ser. No. 13/633,423, filed Oct. 2, 2012, now U.S. Pat. No. 9,273,175. This Application also claims the benefit of U.S. Application No. 61/542,405 filed, on Oct. 3, 2011. The disclosure of application Ser. No. 13/633,423 and 61/542,405 are hereby incorporated by reference.

BACKGROUND OF THE INVENTION

The subject matter of the instant invention relates to a method and composition obtained by contacting a tertiary amine with at least one inert gas. The tertiary amine composition can be used, for example, to produce polyurethane foam having reduced missions.

Tertiary amines are commonly used as catalysts for the preparation of polyurethane materials that are widely used in consumer durable goods (such as cars, home appliances, furniture, toys, among other products) as well as in insulation of commercial and residential areas. Minimization of chemical emissions in these applications is of key importance to eliminate potential exposure of workers and end users to the hazards associated by either adventitious contaminants or by-products produced by adventitious contaminants that may be present in some of the raw materials utilized in the preparation of polyurethane based products. Controlling the presence of undesired contaminants in the raw materials utilized to make polyurethane catalysts is an ongoing challenge because removal of very small amount of impurities from these raw materials is extremely difficult to achieve using conventional separation methods such as chromatography, distillation or recrystallization. Most of these techniques if successfully applied will require extensive labor and time making these methods in many instances cost prohibited. During the preparation of polyurethane foam several components are used such as polyol, isocyanates, surfactants, blowing agents, crosslinkers, cell openers, pigments, fillers, fire retardants, metal catalysts and tertiary amine catalysts. In some cases, certain tertiary amines may contain very small amounts (ppm levels) of contaminants such as formaldehyde and dimethylformamide (DMF). The concentration of these contaminants may increase over relatively long periods of time depending on the storage conditions.

Conventional methods for removing undesired contaminants are disclosed in the following patents. Referring now to one of those patents, U.S. Pat. No. 4,801,426 relates to a method to de-odorize malodorous aliphatic amines by flushing the amine with nitrogen gas at about 30 to 100° C. to remove odorous compounds. The method is conducted on higher aliphatic amines containing long aliphatic chains in the range from $C_8$ to $C_{40}$.

U.S. Pat. No. 7,879,928 discloses a process for preventing the formation of aldehydic compounds in polyether polyols, polyester polyols, or polyurethanes by the incorporation of an effective amount of a phenolic antioxidant and an aminic antioxidant. The process relies upon the addition of chemicals to the polyols or polyurethanes as well as aminic compounds that can also decompose or create undesired emissions from finished products.

U.S. Pat. No. 7,169,268 discloses a process for providing tertiary amine products which are color stable and have greatly reduced tendency to take on color during their storage. The process relies on the addition of ethylene diamines to the distillation pot prior to or during the distillation of the tertiary amine product. This process does not address the formation of color-free contaminants such as dimethylformamide or formaldehyde during storage. Instead, the process is limited to minimizing or reducing color bodies formation overtime that are caused by the presence of impurities in the tertiary amines that can potentially be scavenged by the ethylenediamine prior or during their distillation.

US2008/0269382 discloses a process for stabilizing organic materials. However, this process does not address the long term stability of a polyurethane additive such as a tertiary amine. Also, the process depends on the addition of new chemicals to the polyurethane formulation which may cause additional undesired emissions.

US2009/0088489 discloses a reactive amine catalyst and in particular diethylaminoethoxyethanol and/or diethylethanolamie in aqueous or organic solutions for use in producing flexible polyurethane foam. However, this disclosure does not address the problem of how to prevent the formation of toxic chemicals such as dimethylformamide and formaldehyde on already existing amine catalysts.

US2011/0009512 relates to tertiary amine catalysts useful in the production of polyurethane foam. However, this disclosure does not address the issue of tertiary amine storage as well as minimization or reduction of dimethylformamide.

WO11084865 discloses a method to reduce the formation of DMF and formaldehyde of samples exposed to air using amine oxidation inhibitors such as free radical scavengers and/or antioxidants to prevent the oxidation of the amine. The disadvantage of the method is that requires the addition of new chemicals to the tertiary amine which may bring additional environmental, health and safety issues to both the tertiary amine as well as to the finished product.

The previously described patent applications, patents and other documents are hereby incorporated by reference.

There is a need in this art for a tertiary amine composition having relatively low amounts of undesired contaminants and for a method to produce an amine composition that is stable during storage and does not form such contaminants.

BRIEF SUMMARY OF THE INVENTION

The instant invention solves problems associated with the prior art by providing a tertiary amine composition and process for making the composition wherein the amine is in equilibrium with an inert gaseous phase. Without wishing to be bound by any theory or explanation, it is believe that when certain tertiary amines are stored in sealed containers in which a liquid tertiary amine phase is in equilibrium with an inert gaseous phase, then the concentration of pollutants such as formaldehyde and dimethylformamide is substantially reduced (e.g., when the materials are stored over long periods of time). Thus, this invention provides a simple and cost effective solution to the problem of preventing formation or reducing the concentration of trace pollutants that may be present in tertiary amine polyurethane catalysts. The composition is obtained by flushing followed by bubbling an inert gas such as nitrogen and more preferentially argon to reduce the concentration of any adventitious contaminants present in the tertiary amine (e.g., free oxygen from air or oxygen reversibly bound to the amine which may have an effect on the long term stability and quality of the tertiary amine catalyst). Furthermore, when the tertiary amine contains a compound containing at least one —$NH_2$ group (such as a primary amine or hydrazine or a hydrazine derivative) also in equilibrium with an inert gas, then further DMF prevention or reduction can take place overtime (storage) to the extent that DMF is or becomes non-detectable when these amines are used in the manufacture of consumer durable goods such as polyurethane foam articles.

One aspect of the invention relates to a composition obtained by contacting at least one tertiary amine with at least one inert gas wherein the catalyst and gas are in equilibrium wherein the partial pressure of oxygen in the amine is less than under ambient conditions.

One aspect of the invention relates to a new amine composition that is obtained when inert gases such as argon or nitrogen are contacted with a tertiary amine by first flushing followed by bubbling of a liquid tertiary amine with an inert gas. The resulting tertiary amine liquid products is allowed to equilibrate with the inert gas phase to provide a stable form of the amine which can be more suitable for use in the manufacture of consumer durable goods. When the amine is produced and stored under the presence of an inert gas, then the finished polyurethane product is characterized by lower or non-detectable emissions of toxic compounds such as DMF or formaldehyde from polyurethane foam.

The inventive composition comprises a liquid amine in equilibrium with a gaseous phase in which the partial pressure of oxygen in the gaseous phase is less than about 160 mmHg (0.21 atm) and preferably less than about 110 mmHg (0.14 atm) and more preferably less than about 30 mmHg (0.04 atm). If the liquid amine phase also contains a compound having at least on —$NH_2$ group from a primary amine or hydrazine, then further prevention or minimization of DMF can occur when the tertiary amine is in equilibrium with the inert gas.

Another aspect of the invention relates to a method of making a polyurethane comprising contacting at least one polyisocyanate with at least one polyol in the presence of a catalytically effective amount of the inventive composition.

A further aspect of the invention relates to a polyurethane foam made by using the inventive method and inventive composition.

The aspects of this invention can be used alone or in combination with each other.

BRIEF DESCRIPTION OF SEVERAL VIEWS OF THE DRAWINGS

FIG. 1 is a schematic of a system that can be used in one aspect of the inventive method for producing the inventive amine composition.

DETAILED DESCRIPTION OF THE INVENTION

The instant invention relates to a method and composition obtained by contacting at least one tertiary amine with at least one inert gas. The tertiary amine catalyst can be in equilibrium with the inert gas. By "equilibrium" it is meant that after contacting (e.g., flushing or bubbling) an inert gas with at least one tertiary amine the partial pressure of oxygen in the amine is less than under ambient conditions and the partial pressure of an inert gas is enhanced.

One aspect of the invention relates to a process for treating or producing a tertiary amine catalyst that can be packed and stored in equilibrium with a gaseous phase composed of an inert gas such as a noble gas or nitrogen. The gaseous phase in equilibrium with the amine is enriched with the an inert gas with a partial pressure higher than about 600 mmHg (0.79 atm) and reduced or depleted in oxygen with a partial pressure lower than about 160 mm Hg (0.21 atm). In some cases, the partial pressure of the inert gas in equilibrium with the amine is higher than about 650 mmHg (>0.85 atm) and more preferentially higher than about 700 mmHg (>0.92 atm). The partial pressure of gas can be measured by utilizing sensors or by other techniques known in this art. For example, it is common practice to measure the partial pressure of oxygen by using an electrochemical sensor. Other methods to measure the concentration of oxygen are partial pressure sensor, Zirconia sensor and paramagnetic measurement.

The amine composition can be obtained by flushing followed by bubbling the tertiary amine with the inert gas with or without stirring for at least several minutes (e.g., for about 5 minutes to about 60 minutes), until the head space (gaseous volume in contact with the liquid tertiary amine) is depleted of oxygen and the composition is allowed to reach equilibrium once the vessel containing the amine is tightly sealed under a slight positive pressure of inert gas.

Referring now to FIG. 1, FIG. 1 is a schematic of one aspect of the inventive method for obtaining the inventive amine composition. The amine composition can be obtained by placing the liquid amine in a suitable container such as glass container, stainless steel pale or drum or any other suitable container made with a material compatible with tertiary amines. There are several possible designs for flushing and bubbling of the inert gas through the liquid amine. For example, in the case of a small glass container (≤1.0 litter) a rubber septum can be utilized to separate the atmospheric air phase from the amine head-space. A syringe connected to a gas source can be used to dispense the inert gas by puncturing the rubber septum with the needle and allowing the gas to bubble throughout the liquid. The needle can also be conveniently connected to a sparging devise that allows all the gas to be uniformly dispersed through the liquid. A second needle reaching only the top of the head-space serves as the outlet for gas. Inert gas can flow at a suitable rate as to allow oxygen to be removed from the liquid amine as well as the head space without over-pressurizing the container. For example, a suitable flow rate could be one in which one volume-container of the inert gas is pass each 5 to 30 minutes. After 5 to 10 volumes of inert gas pass through the system the outlet needle is removed followed by the inlet needle. The liquid sample is then allowed to reach equilibrium. A similar procedure can also be followed with a pale or a drum or any type of container. In the case of a drum, inert gas can be passed through a sparging tube as described above followed by capping and sealing of the drum.

The inventive composition can be stored for a long period of time (e.g., at least about 6 months) and it can be used in the manufacture of polyurethane foam. Further reduction of DMF can also be achieved when the liquid phase containing the tertiary amine in equilibrium with the inert gas also contains a compound containing at least one —$NH_2$ functional group as in the case of primary amines or hydrazine or hydrazine derivatives.

In one aspect of the invention, the inventive catalyst (and any foam formulation and foam produced using the inventive catalyst) is substantially free of anti-oxidants such as phenolic and aminic antioxidants. By "substantially free" of antioxidants, it is meant that the catalyst, foam formulation and resultant foam contain less than about 5 ppm and typically about <1 ppm of such antioxidants. This aspect of the invention can overcome problems associated with conventional practices that can be caused by the addition of such antioxidants (e.g., emissions from a foam made with an antioxidant containing formulation).

In one aspect of the invention, the inventive catalyst (and any foam formulation and foam produced using the inventive catalyst) is substantially free of DMF, formaldehyde, among other undesired contaminants. By "substantially free" it is meant that the catalyst, foam formulation and resultant foam contain less than about 10 ppm and typically about ≤1.0 ppm of such contaminants.

One aspect of the invention relates to a method for making polyurethane foams by using the inventive amine catalysts. Examples are given below of TDI and MDI based polyurethane foam formulations which were used to evaluate the inventive amine catalyst in equilibrium with the inert gas. In the case of flexible molded foams, the pads were removed from the heated mold and allowed to cool down to room temperature to monitor dimensional stability (shrinkage) or mechanically crushed to evaluate their physical and mechanical properties.

Hand Mix Evaluations

Hand mix experiments were conducted using the following procedure. Formulations were blended together for approximately 10 minutes using a mechanical mixer equipped with a 7.6 cm diameter high shear mixing blade, rotating at 5000 rpm. Premixed formulations were maintained at 23 C using a low temperature incubator. Mondur TD-80 (an 80/20 2,4/2,6 isomer blend of toluene diisocyanate) or modified MDI was added to the premix at the correct stoichiometric amount for the reported index of each foam. The mixture was blended together with Premier Mill Corporation Series 2000, Model 89, and dispersed for approximately five seconds. The foaming mixture was transferred to an Imperial Bondware #GDR-170 paper bucket and allowed to free rise while data was recorded.

Machine Evaluations

Machine runs for the flexible molded foam were conducted on a Hi Tech Sure Shot MHR-50, cylinder displacement series and high-pressure machine. Fresh premixes, consisting of the appropriate polyols, water, crosslinker, surfactants and catalysts for each formulation were charged to the machine. Mondur TD-80 was used throughout the entire study. All chemical temperatures were held at 23° C. via the machine's internal temperature control units. Foam pours were made into an isothermally controlled, heated aluminum mold maintained at 63° C. The mold was a typical physical property tool designed with internal dimensions of 40.6 cm×40.6 cm×10.2 cm. The mold has five vents, each approximately 1.5 mm in diameter, centered in each corner 10.0 cm from each edge and the geometric center of the lid. The mold was sprayed with a solvent-based release agent, prior to every pour and allowed to dry for one minute before pouring. The foam premix was puddle poured into the center of the mold with a wet chemical charge weight capable of completely filling the mold and obtaining the desired core densities reported. Minimum fill requirements were established for each formulation evaluated. The foam article was demolded at 240 seconds (4 minutes) after the initial pour (detailed in next paragraph). Upon demold, the foam was placed through a mechanical crusher or tested for Force-to-Crush (FTC) measurements or allow to cool down to determine dimensional stability (detailed below). Foam physical properties of each catalyst set were mechanically crushed 1 minute after demold using a Black Brothers Roller crusher set to a gap of 2.54 cm. Crushing was conducted three times on each part, rotating the foam 90 degrees after each pass through the rollers. All parts produced for physical testing were allowed to condition for at least seven days in a constant temperature and humidity room (23° C., 50% relative humidity).

FTC measurements were conducted 45 seconds after demold. The pad was removed from the mold, weighed and placed in the FTC apparatus. The force detection device is equipped with a 2.2 kg capacity pressure transducer mounted between the 323 cm2 circular plate cross head and the drive shaft. The actual force is shown on a digital display. This device mimics the ASTM D-3574, Indentation Force Deflection Test and provides a numerical value of freshly demolded foam's initial hardness or softness. The pad was compressed to 50 percent of its original thickness at a cross-head velocity of 275 mm per minute with the force necessary to achieve the highest compression cycle recorded in Newton's. Ten compression cycles were completed. A cycle takes approximately 30 seconds to complete.

Preparation of Foams

Foams of any of the various types known in the art may be made using the methods of this invention, using typical polyurethane formulations. For example, flexible polyurethane foams with excellent physical properties described herein will typically comprise the components shown below in Table 1, in the amounts indicated. The components shown in Table 1 will be discussed in detail below.

TABLE 1

Polyurethane Components

| Component | Pphp |
|---|---|
| Polyol | 20-100 |
| Polymer polyol | 0-80 |
| Natural oil polyol | Varied |
| Silicone surfactant | 0.5-10 |
| Blowing agent | 2-4.5 |
| Crosslinker | 0.5-2.0 |
| Catalyst | 0.25-10 |
| Isocyanate index | 70-115 |

The amount of polyisocyanate used in polyurethane formulations according to the invention is not limited, but it will typically be within those ranges known to those of skill in the art. An exemplary range is given in table 1, indicated by reference to "NCO Index" (isocyanate index). As is known in the art, the NCO index is defined as the number of equivalents of isocyanate, divided by the total number of equivalents of active hydrogen, multiplied by 100. The NCO index is represented by the following formula. NCO index=[NCO/(OH+NH)]*100.

Flexible foams typically use copolymer polyols as part of the overall polyol content in the foam composition, along with base polyols of about 4000-5000 weight average molecular weight and hydroxyl number of about 28-35. Base polyols and copolymer polyols will be described in detail later herein.

Catalysts

The catalyst of the present invention comprises any tertiary amine that has been stored and maintained in equilibrium with a gas phase rich in an inert gas (e.g., a tertiary amine produced in accordance with the inventive method). Tertiary amine catalysts can contain an isocyanate-reactive group or not. Isocyanate reactive groups comprise primary amine, secondary amine, hydroxyl group, amide or urea. Tertiary amine catalysts containing isocyanate reactive groups include both gelling and blowing catalysts. Exemplary gelling catalysts include at least one member selected from the group consisting of N,N-bis(3-dimethylaminopropyl)-N-isopropanolamine; N,N-dimethylaminoethyl-N'-methyl ethanolamine (DABCO® T, Air Products and Chemicals, Inc. of Allentown, Pa.); N,N,N'-trimethylamino-propyl ethanolamine (POLYCAT® 17, by Air Products and Chemicals, Inc.), N,N-dimethylethanolamine (DABCO® DMEA); N,N-dimethyl-N',N'-2-hydroxy(propyl)-1,3-propylenediamine; dimethylaminopropylamine (DMAPA); (N,N-dimethylaminoethoxy)ethanol, methyl-hydroxy-ethyl-piperazine, bis(N,N-dimethyl-3-aminopropyl)amine (POLYCAT® 15), N,N-dimethylaminopropyl urea (DABCO® NE1060, DABCO® NE1070), N,N'-bis(3-dimethylaminopropyl) urea (DABCO® NE1070, DABCO® NE1080), bis(dimethylamino)-2-propanol, N-(3-aminopropyl)imidazole, N-(2-hydroxypropyl)imidazole, and N-(2-hydroxyethyl) imidazole.

Exemplary blowing catalysts containing isocyanate reactive groups include at least one member selected from the group consisting of 2-[N-(dimethylaminoethoxyethyl)-N-methylamino]ethanol, N,N-dimethylaminoethyl-N'-methyl-N'-ethanol (DABCO®-T), dimethylaminoethoxyethanol and N,N,N'-trimethyl-N'-3-aminopropyl-bis(aminoethyl) ether (DABCO® NE300).

The catalyst may also comprise tertiary amines that are highly volatile and not isocyanate-reactive. Suitable volatile gelling catalysts may include, for example, at least one member selected from the group consisting of diazabicyclooctane (triethylenediamine), supplied commercially as DABCO®33-LV catalyst, tris(dimethyalminopropyl)amine (Polycat® 9), dimethylaminocyclohexylamine (Polycat® 8) and bis(dimethylaminopropyl)-N-methylamine (Polycat® 77), N,N-dimethylcyclohexylamine (Polycat-8, Air Products and Chemicals, Inc. of Allentown, Pa.), N-Methyldicyclohexylamine (Polycat-12, Air Products and Chemicals, Inc. of Allentown, Pa.). Suitable volatile blowing catalysts include, for example, at least one member selected from the group consisting of bis-dimethylaminoethyl ether, commercially supplied as DABCO® BL-11 catalyst by Air Products and Chemicals, Inc.; as well as pentamethyldiethylenetriamine (POLYCAT® 5, Air Products and Chemicals, Inc.), hexamethyltriethylenetetramine, heptamethyltetraethylenepentamine and related compositions; higher permethylated polyamines; 2-[N-(dimethylaminoethoxyethyl)-N-methylamino]ethanol and related structures; alkoxylated polyamines; imidazole-boron compositions; or amino propyl-bis(amino-ethyl)ether compositions. The catalyst compositions may also include other components, for example transition metal catalysts such as organotin compounds.

Typically, the loading of non-fugitive tertiary amine catalyst(s) for making foam according to the invention will be in the range of about 0.1 to about 20 pphp, more typically about 0.1 to about 10 pphp, and most typically about 0.1 to about 5 pphp. However, any effective amount may be used. The term "pphp" means parts per hundred parts polyol. The amount of volatile amine catalyst in the foam formulation can range from about 0.05 to about 20 pphp.

Organic Isocyanates

Suitable organic isocyanate compounds include, but are not limited to, at least one member from the group consisting of hexamethylene diisocyanate (HDI), phenylene diisocyanate (PDI), toluene diisocyanate (TDI), and 4,4'-diphenylmethane diisocyanate (MDI). In one aspect of the invention, 2,4-TDI, 2,6-TDI, or any mixture thereof is used to produce polyurethane foams. Other suitable isocyanate compounds are diisocyanate mixtures known commercially as "crude MDI." One example is marketed by Dow Chemical Company under the name PAPI, and contains about 60% of 4,4'-diphenylmethane diisocyanate along with other isomeric and analogous higher polyisocyanates. The isocyanate index can range from about 80 to about 500 depending on the type of foam formulation. For example, flexible foams have typically an isocyanate index of 80 to 120 while rigid foams such as those typically used in appliances, lamination and spray foam application can have indexes in the range of 100 to 500 depending on the application. The higher indexes are commonly used with trimerization catalyst to produce PIR foams normally used in foam laminates that require good fire performance.

Polyol Component

Polyurethanes are produced by the reaction of organic isocyanates with the hydroxyl groups in a polyol, typically a mixture of polyols. The polyol component of the reaction mixture includes at least a main or "base" polyol. Base polyols suitable for use in the invention include, as non-limiting examples, at least one member selected from the group consisting of polyether polyols. Polyether polyols include poly(alkylene oxide) polymers such as poly(ethylene oxide) and poly(propylene oxide) polymers and copolymers with terminal hydroxyl groups derived from polyhydric compounds, including diols and triols. Examples of diols and triols for reaction with the ethylene oxide or propylene oxide include at least one member selected from the group consisting of ethylene glycol, propylene glycol, 1,3-butanediol, 1,4-butanediol, 1,6-hexanediol, neopentyl glycol, diethylene glycol, dipropylene glycol, pentaerythritol, glycerol, diglycerol, trimethylol propane, and similar low molecular weight polyols. Other base polyol examples known in the art include polyhydroxy-terminated acetal resins, hydroxyl-terminated amines and hydroxyl-terminated polyamines. Examples of these and other suitable isocyanate-reactive materials may be found in U.S. Pat. No. 4,394,491; the disclosure of which is hereby incorporated by reference. Suitable polyols also include those containing tertiary amine groups than can catalyze the gelling and the blowing reaction of polyurethanes, for example those described in WO 03/016373 A1, WO 01/58976 A1; WO2004/060956 A1; WO03/016372 A1; and WO03/055930 A1; the disclosure of the foregoing is hereby incorporated by reference. Other useful polyols may include polyalkylene carbonate-based polyols and polyphosphate-based polyols. The amount of polyether polyol can range from about 20 to about 100 pphp of the foam formulation.

In one aspect of the invention, a single high molecular weight polyether polyol may be used as the base polyol. Alternatively, a mixture of high molecular weight polyether polyols, for example, mixtures of di- and tri-functional materials and/or different molecular weight or different chemical composition materials may be used. Such di- and tri-functional materials include, but are not limited to at least one member selected from the group consisting of polyethylene glycol, polypropylene glycol, glycerol-based polyether triols, trimethylolpropane-based polyether triols, and other similar compounds or mixtures, provided that they are ester-free. In some embodiments of the invention, at least about 50 wt % of the ester-free polyol component consists of one or more polyether polyols.

In addition to the base polyols described above, or instead of them, materials commonly referred to as "copolymer polyols" may be included in a polyol component for use according to the invention. Copolymer polyols may be used in polyurethane foams to increase the resistance of the foam to deformation, for example to improve the load-bearing properties of the foam. Depending upon the load-bearing requirements for the polyurethane foam, copolymer polyols may comprise from 0 to about 80 percent by weight of the total polyol content. Examples of copolymer polyols include, but are not limited to, graft polyols and polyurea modified polyols, both of which are known in the art and are commercially available.

Graft polyols are prepared by copolymerizing vinyl monomers, typically styrene and acrylonitrile, in a starting polyol. The starting polyol is typically a glycerol-initiated triol, and is typically end-capped with ethylene oxide (approximately 80-85% primary hydroxyl groups). Some of the copolymer grafts to some of the starting polyol. The graft polyol also contains homopolymers of styrene and acrylonitrile and unaltered starting polyol. The styrene/acrylonitrile solids content of the graft polyol typically ranges from about 5 wt % to about 45 wt %, but any kind of graft polyol known in the art may be used.

Polyurea modified polyols are formed by the reaction of a diamine and a diisocyanate in the presence of a starting polyol, with the product containing polyurea dispersion. A variant of polyurea modified polyols, also suitable for use, are polyisocyanate poly addition (PIPA) polyols, which are formed by the in situ reaction of an isocyanate and an alkanolamine in a polyol.

Useful polyester polyol include those produced when a dicarboxylic acid is reacted with an excess of a diol for example adipic acid or phathalic acid or phthalic anhydride with ethylene glycol or butanediol or reacting a lactone with an excess of a diol such as caprolactone with propylene glycol. Mannich polyols are also typically used in spray formulations. Mannich polyols are made by the condensation of phenols with aldehydes and amines to give polyols containing multiple hydroxyl groups (2 to 8) and tertiary amine centers. Polyester polyols can normally be present from about 0 to about 100 pphp.

Natural Oil Polyol Component

All or a portion of the polyols useful in the preparation of polyurethane foam from inexpensive and renewable resources are highly desirable to minimize the depletion of fossil fuel and other non-sustainable resources. Natural oils consist comprise triglycerides of saturated and unsaturated fatty acids. One natural oil polyol is castor oil, a natural triglyceride of ricinoleic acid which is commonly used to make polyurethane foam even though it has certain limitations such as low hydroxyl content. Other natural oils need to be chemically modified to introduce sufficient hydroxyl content to make them useful in the production of polyurethane polymers. There are two chemically reactive sites that can be considered when attempting to modify natural oil or fat into a useful polyol: 1) the unsaturated sites (double bonds); 2) the ester functionality. Unsaturated sites present in oil or fat can be hydroxylated via epoxidation/ring opening or hydroformilation/hydrogenation. Alternatively, trans-esterification can also be utilized to introduce OH groups in natural oil and fat. The chemical process for the preparation of natural polyols using epoxidation route involves a reaction mixture that requires epoxidized natural oil, a ring opening acid catalyst and a ring opener. Epoxidized natural oils include epoxidized plant-based oils (epoxidized vegetable oils) and epoxidized animal fats. The epoxidized natural oils may be fully or partially epoxidized and these oils include at least one member selected from the group consisting of soybean oil, corn oil, sunflower oil, olive oil, canola oil, sesame oil, palm oil, rapeseed oil, tung oil, cotton seed oil, safflower oil, peanut oil, linseed oil and combinations thereof. Animal fats include fish, tallow and lard. These natural oils are triglycerides of fatty acids which may be saturated or unsaturated with various chain lengths from $C_{12}$ to $C_{24}$. These acids can be: 1) saturated: lauric, myristic, palmitic, steric, arachidic and lignoceric; 2) mono-unsaturated: palmitoleic, oleic, 3) poly-unsaturated: linoleic, linolenic, arachidonic. Partially or fully epoxidized natural oil may be prepared when reacting peroxyacid under suitable reaction conditions. Examples of peroxyacids utilized in the epoxidation of oils have been described in WO 2006/116456 A1; the disclosure of which is hereby incorporated by reference. Ring opening of the epoxidized oils with alcohols, water and other compounds having one or multiple nucleophilic groups can be used. Depending on the reaction conditions oligomerization of the epoxidized oil can also occur. Ring opening yields natural oil polyol that can be used for the manufacture of polyurethane products. In the hydroformilation/hydrogenation process, the oil is hydroformylated in a reactor filled with a hydrogen/carbon monoxide mixture in the presence of a suitable catalyst (typically cobalt or rhodium) to form an aldehyde which is hydrogenated in the presence of cobalt or nickel catalyst to form a polyol. Alternatively, polyol form natural oil and fats can be produced by trans-esterification with a suitable poly-hydroxyl containing substance using an alkali metal or alkali earth metal base or salt as a trans-esterification catalyst. Any natural oil or alternatively any partially hydrogenated oil can be used in the transesterification process. Examples of oils include but are not limited to at least one member selected from the group consisting of soybean, corn, cottonseed, peanut, castor, sunflower, canola, rapeseed, safflower, fish, seal, palm, tung, olive oil or any blend. Any multifunctional hydroxyl compound can also be used such as lactose, maltose, raffinose, sucrose, sorbitol, xylitol, erythritol, mannitol, or any combination. The amount of natural oil polyol can range from about 0 to about 40 pphp of the foam formulation.

Blowing Agents

Polyurethane foam production may be aided by the inclusion of a blowing agent to produce voids in the polyurethane matrix during polymerization. Any blowing agent known in the art may be used. Suitable blowing agents include compounds with low boiling points which are vaporized during the exothermic polymerization reaction. Such blowing agents are generally inert and therefore do not decompose or react during the polymerization reaction. Examples of inert blowing agents include, but are not limited to, at least one member selected from the group consisting of carbon dioxide, chlorofluorocarbons, hydrogenated fluorocarbons, hydrogenated chlorofluorocarbons, fluoroolefins, chlorofluoroolef ins, hydrofluoroolef ins, hydrochlorfluoro olefins, acetone, and low-boiling hydrocarbons such as cyclopentane, isopentane, n-pentane, and their mixtures. Other suitable blowing agents include compounds, for example water, that react with isocyanate compounds to produce a gas. The amount of blowing agent is typically from about 0 (water blown) to about 80 pphp. Water (blow foam by reacting with isocyanate making $CO_2$) can be present in the range from about 0 (if a BA is included) to about 60 pphp (a very low density foam) and typically from about 1.0 pphp to about 10 pphp and, in some cases, from about 2.0 pphp to about 5 pphp.

Other Optional Components

A variety of other components or ingredients may be included in the formulations for making foams according to the invention. Examples of optional components include, but are not limited to, at least one member selected from the group consisting of cell stabilizers, crosslinking agents, chain extenders, pigments, fillers, flame retardants, auxiliary urethane gelling catalysts, auxiliary urethane blowing catalysts, transition metal catalysts, and combinations of any of these. Cell stabilizers can used in an amount from about 0.1 to about 20 pphp and typically from about 0.1 to about 10 pphp and, in some cases, from about 0.1 to about 5.0 pphp. Fire retardants can be used in an amount from about 0 to about 20 pphp and from about 0 to about 10 pphp and from about 0 to about 5 pphp.

Cell stabilizers may include, for example, silicone surfactants or anionic surfactants. Examples of suitable silicone surfactants include, but are not limited to, at least one member from the group consisting of polyalkylsiloxanes, polyoxyalkylene polyol-modified dimethylpolysiloxanes, alkylene glycol-modified dimethylpolysiloxanes, or any combination thereof. Suitable anionic surfactants include, but are not limited to, salts of fatty acids, salts of sulfuric acid esters, salts of phosphoric acid esters, salts of sulfonic acids, and combinations of any of these.

Crosslinking agents include, but are not limited to, at least one member selected from the group consisting of low-molecular weight compounds containing at least two moieties selected from hydroxyl groups, primary amino groups, secondary amino groups, and other active hydrogen-containing groups which are reactive with an isocyanate group. Crosslinking agents include, for example, at least one member selected from the group consisting of polyhydric alcohols (especially trihydric alcohols, such as glycerol and trimethylolpropane), polyamines, and combinations thereof. Non-limiting examples of polyamine crosslinking agents include diethyltoluenediamine, chlorodiaminobenzene, diethanolamine, diisopropanolamine, triethanolamine, tripropanolamine, 1,6-hexanediamine, and combinations thereof. Typical diamine crosslinking agents comprise twelve carbon atoms or fewer, more commonly seven or fewer. The amount of crosslinking agent typically ranges from about 0.1 pphp to about 20 pphp Examples of chain extenders include, but are not limited to, compounds having hydroxyl or amino functional group, such as glycols, amines, diols, and water. Specific non-limiting examples of chain extenders include at least one member selected from the group consisting of ethylene glycol, diethylene glycol, propylene glycol, dipropylene glycol, 1,4-butanediol, 1,3-butanediol, 1,5-pentanediol, neopentyl glycol, 1,6-hexanediol, 1,10-decanediol, 1,12-dodecanediol, ethoxylated hydroquinone, 1,4-cyclohexanediol, N-methylethanolamine, N-methylisopropanolamine, 4-aminocyclohexanol, 1,2-diaminoethane, 2,4-toluenediamine, or any mixture thereof.

Pigments may be used to color code the polyurethane foams during manufacture, for example to identify product grade or to conceal yellowing. Pigments may include any suitable organic or inorganic pigments known in the polyurethane art. For example, organic pigments or colorants include, but are not limited to, at least one member selected from the group consisting of azo/diazo dyes, phthalocyanines, dioxazines, and carbon black. Examples of inorganic pigments include, but are not limited to, titanium dioxide, iron oxides, or chromium oxide. The amount of any pigment typically ranges from about 0 pphp to about 15 pphp.

Fillers may be used to increase the density and load bearing properties of polyurethane foams. Suitable fillers include, but are not limited to, barium sulfate or calcium carbonate. The amount of any filler typically ranges from about 0 pphp to about 30 pphp Flame retardants may be used to reduce the flammability of polyurethane foams. For example, suitable flame retardants include, but are not limited to, chlorinated phosphate esters, chlorinated paraffins, or melamine powders.

Certain aspects of the invention are demonstrated by the following Examples which are provided only to illustrate certain aspects of the invention and shall not limit the scope of the claims appended hereto.

Example 1

Tertiary Amine Compositional Changes with Time when the Tertiary Amine is Stored in Equilibrium with a Headspace Volume Composed of Atmospheric Air The model tertiary N,N,N'-trimethyl-N'-3-aminopropyl-bis(aminoethyl) ether (amine-1) was selected for this study because this compound is widely used as a blowing catalyst in many commercial applications. The catalyst is a blowing polyurethane catalyst commonly used in flexible molded and flexible slabstock applications where chemical emanation is of great concern. However, the catalyst is also employed in many other used such as rigid, semi-rigid, spray and any other application where water may be used to blow the polyurethane polymer. In this example, 19 ml of amine-1 was placed in a 25 ml vial and the amine liquid phase was conditioned at 55° C. with the remaining 6 ml of the vial occupied by atmospheric air in equilibrium with the liquid amine phase. The vial was open after 15 days to take a sample for analysis (sample #1). The vial was closed and reconditioned at 55° C. for an additional 15 days after which a second sample was taken for analysis (sample #2). The results show that large increase in the concentration of formaldehyde and DMF are observed when the liquid amine is in equilibrium with air.

TABLE 1

Formaldehyde and DMF concentrations

| Temperature (° C.)/Sample # | Equilibrium gas | Time (days) | DMF (ppm) | Formaldehyde (ppm) |
|---|---|---|---|---|
| 55/#1 | Air | 15 | 14 | 238 |
| 55/#2 | Air | 30 | 30 | 340 |

Example 2

Tertiary Amine Compositional Changes with Time when the Tertiary Amine is Stored in Equilibrium with a Headspace Volume Composed of a Nitrogen Enriched Atmosphere Amine-1 (19 ml) was placed in a 25 ml vial and the liquid was flushed with nitrogen for 15 minutes until the 6 ml head space (gaseous volume in contact with the liquid tertiary amine) was depleted of oxygen. The composition was allowed to reach equilibrium once the vial containing the amine was tightly sealed under a slight positive pressure of nitrogen. The vial was open after 15 days to take a sample for analysis (sample #3). The vial was closed and reconditioned at 55° C. for an additional 15 days after which a second sample was taken for analysis (sample #4). The result shows that some increase in the concentration of formaldehyde and DMF is still observed but the final concentration of DMF and formaldehyde is significantly lower than in example 1 where the sample was allow to reach equilibrium under air. Thus, examples 1 and 2 illustrate that oxygen plays a role in increasing the concentration of DMF and formaldehyde because when the sample is placed under a nitrogen rich atmosphere then the final concentration of DMF and formaldehyde is substantially smaller.

TABLE 2

| Formaldehyde and DMF concentrations | | | | |
|---|---|---|---|---|
| Temperature (° C.)/Sample # | Equilibrium gas | Time (days) | DMF (ppm) | Formaldehyde (ppm) |
| 55/#3 | Nitrogen | 15 | 7 | 75 |
| 55/#4 | Nitrogen | 30 | 16 | 122 |

Example 3

Tertiary Amine Compositional Changes with Time when the Tertiary Amine is Stored in Equilibrium with a Different Headspace Volume Composed of Atmospheric Air Amine-1 was placed in a vial and the volume of the headspace having atmospheric air in equilibrium with the amine phase was varied to see the effect that a larger amount of oxygen on the headspace would have on the concentration of DMF and formaldehyde as the sample is conditioned at 55° C. over a long period of time. The results shown in table 3 illustrates that a sample in equilibrium with more air for 20 days had more DMF and formaldehyde than a sample conditioned for 39 days with less air (<6 ml air). This example illustrates that the amount of oxygen present on the headspace plays a role on the final concentration of DMF and formaldehyde in the liquid phase. A headspace composed mainly of nitrogen or an inert gas result in little or no appreciable change in the concentration of DMF and formaldehyde.

TABLE 3

| Formaldehyde and DMF concentrations | | | | | |
|---|---|---|---|---|---|
| Temperature (° C.) | Equilibrium gas | Time (days) | Headspace volume (ml) | DMF (ppm) | Formaldehyde (ppm) |
| 55 | Air | 0 | — | 10 | 60 |
| 55 | Air | 20 | ~6 ml | 78 | 708 |
| 55 | Air | 39 | <6 ml | 44 | 554 |

Example 4

This Example Shows that Amine-1 has No Significant Compositional Changes when Antioxidant (Benzenepropanoic Acid, 3,5-bis (1,1-dimethylethyl)-4-hydroxy-.C7-C9 Branched Alkyl Esters) is Added to the Amine Liquid Phase Amine-1 (19 ml) was placed in a 25 ml vial and the volume of the headspace was first flushed and then bubbled with either nitrogen or air depending on the sample to create and maintain a gaseous phase in equilibrium with the amine liquid phase. The antioxidant containing solutions were prepared by dilution method and 6 vial samples were prepared for 6 months ageing of each sample under same condition. All samples were conditioned at 55° C. and one vial was removed after about a month to analyze for DMF and HCHO. The results are shown in table 4 & 5. Surprisingly, it was found that when the solution is kept in equilibrium the total concentration of formaldehyde does not show an appreciable change in concentration overtime whether there is antioxidant or not even when the sample was initially placed in equilibrium with air. The sample placed initially in equilibrium with air showed higher formaldehyde concentration than the sample in equilibrium with nitrogen. However, over a long period of time the presence or absence of antioxidant did not have a statistically significant effect on reducing the concentration of formaldehyde. Without wishing to be bound by any theory or explanation, it is believed that oxidation does eventually takes place or the formation of an amine-oxygen species is too fast for an antioxidant to compete since its concentration ought to be small. Thus, an effective way to prevent the formation of formaldehyde is by flushing and then bubbling nitrogen over a period of time sufficient to remove all forms of $O_2$ from the system. Most surprisingly was the finding that the concentration of DMF actually decreases with time even when the sample was initially conditioned with air and that the presence of antioxidant had no effect on this reduction. A similar case (Table 6) is observed with other antioxidants such as octadecyl-3-(3,5-di-tert.butyl-4-hydroxyphenyl)-propionate and vitamin E.

TABLE 4

| DMF concentrations | | | | | | | | |
|---|---|---|---|---|---|---|---|---|
| DMF Anti - oxidant | ppm | Benzenepropanoic acid, 3,5-bis (1,1-dimethyl-ethyl)-4-hydroxy-.C7-C9 branched alkyl esters | | | | | | |
| Temp | ° C. | | | | 55 | | | |
| Time | Day | 0 | 16 | 44 | 72 | 100 | 135 | 170 |
| $N_2$ | 5,000 | 3.5 | 2.0 | 1.7 | 1.2 | 1.0 | 1.0 | #### |
| | 1,000 | | 1.9 | 1.8 | 1.0 | 1.0 | 1.0 | #### |
| | 500 | | 1.5 | 1.0 | 1.0 | 1.0 | 1.1 | 1.0 |
| | 0 | | 3.8 | 1.6 | 1.0 | 1.0 | 1.0 | 1.0 |
| Air | 1,000 | 3.5 | 2.5 | 1.2 | 1.0 | 1.0 | 1.2 | 1.0 |
| | 0 | | 6.6 | 1.8 | 1.1 | 1.0 | 1.2 | 1.0 |

TABLE 5

| Formaldehyde concentrations | | | | | | | | |
|---|---|---|---|---|---|---|---|---|
| HCHO Anti- oxidant | ppm | Benzenepropanoic acid, 3,5-bis (1,1-dimethyl-ethyl)-4-hydroxy-.C7-C9 branched alkyl esters | | | | | | |
| Temp | ° C. | | | | 55 | | | |
| Time | Day | 0 | 16 | 44 | 72 | 100 | 135 | 170 |
| $N_2$ | 5,000 | 62 | 57 | 69 | 71 | 74 | 80 | 84 |
| | 1,000 | | 59 | 73 | 75 | 78 | 80 | 85 |
| | 500 | | 61 | 80 | 72 | 72 | 77 | 78 |
| | 0 | | 57 | 72 | 72 | 76 | 73 | 75 |
| Air | 1,000 | 62 | 107 | 119 | 118 | 99 | 114 | 113 |
| | 0 | | 97 | 112 | 104 | 107 | 108 | 100 |

TABLE 6

DMF concentrations when using octadecyl-3-(3,5-di-tert.butyl-4-hydroxyphenyl)-propionate and Vitamin E

| DMF Anti-oxidant | ppm | octadecyl-3-(3,5-di-tert.butyl-4-hydroxyphenyl)-propionate | | | | | | | Vitamin E | | | | | | |
|---|---|---|---|---|---|---|---|---|---|---|---|---|---|---|---|
| Temp | ° C. | 55 | | | | | | | RT (~25) | | | | | | |
| Time | Day | 0 | 16 | 44 | 72 | 100 | 135 | 170 | 0 | 16 | 44 | 72 | 100 | 135 | 170 |
| $N_2$ | 5,000 | 3.5 | 1.0 | 1.0 | 1.0 | 1.0 | 1.0 | 1.0 | 3.5 | 1.4 | 1.0 | 1.0 | 1.0 | 1.0 | 1.0 |
| | 1,000 | | 1.0 | 1.0 | 1.0 | 1.0 | 1.0 | 1.0 | | 1.0 | 1.0 | 1.0 | 1.0 | 1.0 | 1.0 |
| | 500 | | 1.8 | 1.0 | 1.5 | 2.7 | 1.0 | 1.0 | | 1.0 | 1.0 | 1.0 | 1.0 | 1.0 | 1.0 |
| $N_2$ | 0 | 3.5 | 3.8 | 1.6 | 1.0 | 1.0 | 1.0 | 1.0 | 3.5 | 3.8 | 1.6 | 1.0 | 1.0 | 1.0 | 1.0 |

Example 5

Argon Gas in Equilibrium with Tertiary Amine is More Efficient at Preventing Compositional Changes than Nitrogen Argon is utilized in a similar manner as nitrogen and samples of amine-1 are flushed and bubbled with argon gas until equilibrium is obtained between gaseous phase and the amine liquid phase. In a 25 ml vial, 19 ml of amine-1 is placed in a 25 ml vial and the amine liquid phase is conditioned at 55° C. with the remaining 6 ml of the vial occupied by argon gas in equilibrium with the liquid amine phase. The vial is open after 15 days to take a sample for analysis (sample #1). The vial is closed and reconditioned at 55° C. for an additional 15 days after which a second sample is taken for analysis (sample #2). The net result is that smaller amount of formaldehyde and DMF is observed when the liquid sample is in equilibrium with argon relative. Thus argon is more effective than nitrogen at preventing the formation of formaldehyde and DMF.

Example 6

Argon Gas in Equilibrium with Tertiary Amine and in the Presence of a —$NH_2$ Containing Molecule to Minimize DMF and Formaldehyde Formation Tertiary amines is flushed and bubbled with argon gas until equilibrium is obtained between gaseous phase and the amine liquid phase. The tertiary amine in this case contains a substance that contains at least one —$NH_2$ functionality such as a primary amine, hydrazine or a hydrazine derivative. In 25 ml vial, 19 ml of amine-1 is placed in a 25 ml vial and the amine liquid phase is conditioned at 55° C. with the remaining 6 ml of the vial occupied by argon gas in equilibrium with the liquid amine phase. The vial is open after 15 days to take a sample for analysis (sample #1). The vial is closed and reconditioned at 55° C. for an additional 15 days after which a second sample is taken for analysis (sample #2). The net result is that further reduction in formaldehyde and DMF is observed when the tertiary amine in equilibrium with argon contains a —$NH_2$ containing substance.

Example 7

Tertiary Amine Compositional Changes with Time when the Tertiary Amine is Stored in Equilibrium with a Headspace Volume Composed of Argon In this example, 19 ml of amine-1 was placed in four different 25 ml vials and the amine liquid phase was conditioned at ambient temperature (25° C.) with the remaining 6 ml of the vial occupied by either atmospheric air (samples 1 and 2) or argon (samples 3 and 4) in equilibrium with the liquid amine phase. The vial was open after 30 days to perform the analysis for DMF content. The initial content of DMF in the sample was 7 ppm. The results shown in Table 7 illustrates that the increase in DMF concentration was significantly reduced when the amine was conditioned with Argon gas.

TABLE 7

DMF concentrations

| Temperature (° C.)/Sample # | Equilibrium Gas | Time (days) | DMF (ppm) |
|---|---|---|---|
| 25/Initial | Air | 0 | 7 |
| 25/#1 | Air | 30 | 27 |
| 25/#2 | Air | 30 | 22 |
| 25/#3 | Argon | 30 | 9 |
| 25/#4 | Argon | 30 | 10 |

Example 8

This Example Shows that Amine-1 can be Used as a Blowing Catalyst to Make Polyurethane Foam with a Wide Variety of Gelling Polyurethane Foam Catalyst Foam pads were prepared by adding a tertiary amine catalyst to about 302 g of a premix (prepared as in Table 8) in a 32 oz (951 ml) paper cup. The formulation was mixed for about 10 seconds at about 6,000 RPM using an overhead stirrer fitted with a 2-inch (5.1 cm) diameter stirring paddle.

The toluene diisocyanate was then added, and the formulation was mixed well for about another 6 seconds at about 6,000 RPM using the same stirrer, after which it was poured into a pre-heated mold at 70° C. and demolded after 4 minutes. The foam pads were removed from the mold, hand crushed, weighed and machine crushed at 75% pad thickness. Foam pads were stored under constant temperature and humidity conditions for 48 hours before being cut and tested.

TABLE 8

PREMIX COMPONENTS

| Component | #1 PPHP |
|---|---|
| SPECFLEX ® NC 630[1] | 50 |
| SPECFLEX ® NC 700[2] | 50 |
| Water | 3.0 |

TABLE 8-continued

| PREMIX COMPONENTS | |
|---|---|
| Component | #1 PPHP |
| DABCO ® DC6070[3] | 0.60 |
| Catalyst | Varied |
| Diethanolamine (crosslinker) | 0.70 |
| Toluene diisocyanate | To provide NCO index = 100 |

[1]High functionality capped polyether polyol of high molecular weight, functionality, and primary hydroxyl content with a base polyol molecular weight of about 5500, available from Dow Chemical Company, Midland, MI
[2]Grafted polyether polyol containing copolymerized styrene and acrylonitrile, base polyol molecular weight about 4800, available from Dow Chemical Company, Midland, MI
[3]Silicone surfactant is available from Air Products and Chemicals, Inc.
[4] The amine catalyst is available from Air Products and Chemicals, Inc.

The toluene diisocyanate was then added, and the formulation was mixed well for about another 6 seconds at about 6,000 RPM using the same stirrer, after which it was poured into a pre-heated mold at 70° C. and demolded after 4 minutes. The foam pads were removed from the mold, hand crushed, weighed and machine crushed at 75% pad thickness. Dimensional stability (foam shrinkage) was evaluated by allowing the foam pads to cool down and observing whether shrinkage or not took place. Foam pads were stored under constant temperature and humidity conditions for 48 hours before being cut and tested.

Table 9 shows physical properties of flexible molded polyurethane foam pads for gelling catalysts with different molecular structures and isocyanate reactive functionalities. The flexible molded pads were made using a single gelling amine catalyst to show the influence of each individual structure on physical properties. The blowing catalyst was in each case was amine-1 (N,N,N'-trimethyl-N'-3-aminopropyl-bis(aminoethyl) ether).

TABLE 9

| PHYSICAL PROPERTIES AT AMBIENT DATA | | | | | | |
|---|---|---|---|---|---|---|
| Catalyst | Tear (lbf) | Tensile (psi) | Elongation (%) | Airflow (SCFM) | 50% CS Height Loss | Density (lb/cuft) |
| Triethylenediamine (1) | 1.63 | 17.4 | 99.3 | 2.31 | 8.21 | 1.89 |
| Bis(dimethylaminopropyl) amine (2) | 1.27 | 14.3 | 82.1 | 1.94 | 11.86 | 1.95 |
| Dimethylaminoethoxyethanol (3) | 1.40 | 15.3 | 151.7 | 1.74 | 6.18 | 1.87 |
| Dimethylaminopropylureas (mono and bis mixture) (4) | 1.26 | 15.0 | 158.9 | 2.12 | 4.96 | 1.84 |
| N,N-bis(dimethylamino propyl)-N-(2-hydroypropyl)amine (5) | 1.54 | 15.7 | 155.8 | 1.78 | 4.83 | 1.86 |
| N-dimethylaminopropyl-N-(2-hydroxyethyl)-N-methylamine (6) | 1.37 | 16.3 | 94.4 | 2.11 | 40.9 | 1.81 |
| N-dimethylaminoethyl-N-(2-hydroxyethyl)-N-methylamine (7) | 1.55 | 17.0 | 105.8 | 2.02 | 43.7 | 1.80 |

While the invention has been described with reference to certain aspects or embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof including usage of these aspects alone or in combination with each other. Therefore, it is intended that the invention not be limited to the particular embodiment disclosed, for example, as the best mode contemplated for carrying out this invention, but that the invention will include all aspects or embodiments falling within the scope of the appended claims.

The invention claimed is:

1. A method of making a polyurethane comprising contacting at least one polyisocyanate with at least one polyol in the presence of a catalytically effective amount of a composition obtained by contacting at least one tertiary amine with at least one inert gas wherein the tertiary amine and gas are in equilibrium, wherein the partial pressure of oxygen in the composition is less than under ambient conditions, wherein the amine contains at least one isocyanate reactive group comprising at least one member selected from the group consisting of secondary amine, hydroxyl, amide, and urea, wherein a concentration of DMF in the composition is less than about 10 parts per million, wherein a concentration of formaldehyde in the composition is less than about 10 parts per million, and wherein a concentration of antioxidants in the composition is less than about 5 parts per million.

2. The method of claim 1, wherein the contacting of the at least one polyisocyanate and the polyol occurs in the presence of at least one blowing agent under conditions sufficient to produce a polyurethane foam.

3. The method of claim 1 wherein the inert gas comprises at least one of nitrogen and argon.

4. The method of claim 3 wherein the inert gas comprises argon.

5. The method of claim 1 wherein the concentration of antioxidants in the composition is less than about 1 parts per million, wherein the concentration of DMF in the composition is less than about 1 parts per million, and wherein the concentration of formaldehyde in the composition is less than about 1 parts per million.

6. The method of claim 1 wherein the contacting of the at least one polyisocyanate and the polyol occurs in the presence of water, at least one crosslinker, and at least one silicone surfactant.

7. The method of claim 1 wherein at least one tertiary amine comprises N,N,N'-trimethyl-N'-3-aminopropyl-bis (aminoethyl) ether.

8. The method of claim 1 wherein the at least one tertiary amine comprises a blowing catalyst.

9. The method of claim 8 further comprising at least one member selected from the group consisting of triethylenediamine, bis(dimethylaminopropyl) amine, dimethylaminoethoxyethanol, dimethylaminopropylureas, N,N-bis(dimethylamino propyl)-N-(2-hydroypropyl)amine, N-dimethylaminopropyl-N-(2-hydroxyethyl)-N-methylamine, and N-dimethylaminoethyl-N-(2-hydroxyethyl)-N-methyl amine.

10. The method of claim 1 wherein the composition comprises at least one liquid tertiary amine catalyst that has been bubbled with at least one inert gas wherein the amine catalyst and gas are in equilibrium and wherein the partial pressure of oxygen in the amine catalyst is less than under ambient conditions and wherein the composition is substantially free of anti-oxidants, DMF and formaldehyde.

11. The method of claim 1 wherein the composition is obtained by contacting at least one liquid tertiary amine catalyst with at least one inert gas wherein the amine catalyst and gas are in equilibrium; wherein the composition is substantially free of anti-oxidants and wherein the partial pressure of inert gas is higher than about 600 mmHg (0.79 atm) and the partial pressure of oxygen is lower than about 160 mm Hg (0.21 atm).

12. The method of claim 1 wherein the tertiary amine catalyst contains at least one isocyanate-reactive group comprising at least one member consisting of primary amine, secondary amine, hydroxyl group, amide and urea.

13. The method of claim 1 wherein the tertiary amine catalyst comprises at least one member selected from the group consisting of N,N-bis(3-dimethylaminopropyl)-N-isopropanolamine; N,N-dimethylaminoethyl-N'-methyl ethanolamine; N,N,N'-trimethylaminopropyl ethanolamine, N,N-dimethylethanolamine; N,N-dimethyl-N',N'-2-hydroxy (propyl)-1,3-propylenediamine; dimethylaminopropylamine; (N,N-dimethylaminoethoxy)ethanol, methyl-hydroxy-ethyl-piperazine, bis(N,N-dimethyl-3-aminopropyl)amine, N,N-dimethylaminopropyl urea, N,N'-bis(3-dimethylamino-propyl) urea, bis(dimethylamino)-2-propanol, N-(3-amino-propyl)imidazole, N-(2-hydroxypropyl)imidazole, and N-(2-hydroxyethyl) imidazole.

14. The method of claim 1 wherein the tertiary amine catalyst comprises at least one member selected from the group consisting of 2-[N-(dimethylaminoethoxyethyl)-N-methylamino]ethanol, N, N-dimethylaminoethyl-N'-methyl-N-ethanol, dimethylaminoethoxyethanol and N,N,N'-trimethyl-N'-3-aminopropyl-bis(aminoethyl) ether.

15. The method of claim 1 wherein the tertiary amine catalyst comprises at least one member selected from the group consisting of diazabicyclooctane, tris(dimethyalmino-propyl)amine, dimethylaminocyclohexylamine, bis(dimethylaminopropyl)-N-methylamine, N,N-dimethylcyclohexyl amine, and N-Methyldicyclohexylamine.

16. The method of claim 1 wherein the tertiary amine catalyst comprises at least one member selected from the group consisting of bis-dimethylaminoethyl ether, pentamethyldiethylenetriamine, hexamethyltriethylenetetramine, heptamethyltetraethylenepentamine, 24N-(dimethylaminoethoxyethyl)-N-methylamino]ethanol, alkoxylated polyamines; imidazole-boron compositions; and amino propyl-bis(amino-ethyl)ether compositions.

17. The method of claim 1 wherein the method further comprising molding a contact product of polyol and polyisocyanate.

18. An article of manufacture comprising the polyurethane foam prepared by the method of claim 17.

* * * * *